(12) United States Patent
Hoffmann et al.

(10) Patent No.: US 8,715,633 B2
(45) Date of Patent: May 6, 2014

(54) COMPOSITION FOR KERATIN FIBRES

(75) Inventors: Martin Hoffmann, Zwingenberg (DE); Iika Tietjen, Sandhausen (DE); Ina Bräutigam, Darmstadt (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/349,117

(22) Filed: Jan. 12, 2012

(65) Prior Publication Data

US 2012/0103357 A1    May 3, 2012

Related U.S. Application Data

(62) Division of application No. 11/938,345, filed on Nov. 12, 2007, now abandoned.

(51) Int. Cl.
*A61Q 5/12* (2006.01)

(52) U.S. Cl.
USPC .................................. 424/70.28; 424/70.27

(58) Field of Classification Search
None
See application file for complete search history.

(56) References Cited

U.S. PATENT DOCUMENTS

| | | | |
|---|---|---|---|
| 4,240,450 A | 12/1980 | Grollier et al. | |
| 4,761,273 A | 8/1988 | Grollier et al. | |
| 4,997,641 A * | 3/1991 | Hartnett et al. | 424/70.122 |
| 5,683,685 A * | 11/1997 | Hirano et al. | 424/78.03 |
| 5,888,251 A | 3/1999 | Fogg et al. | |
| 6,709,648 B2 | 3/2004 | Sako et al. | |
| 2005/0169864 A1 * | 8/2005 | Derici et al. | 424/70.11 |

FOREIGN PATENT DOCUMENTS

| | | |
|---|---|---|
| DE | 2521960 | 4/1976 |
| DE | 2811010 | 9/1978 |
| DE | 3044738 A1 | 6/1981 |
| DE | 3217059 | 11/1982 |
| EP | 337354 | 10/1989 |
| EP | 0 524 612 | 1/1993 |
| EP | 0 640 643 | 3/1995 |
| EP | 0 996 408 | 6/2006 |
| GB | 1513672 | 6/1978 |
| WO | 02/060397 | 8/2002 |
| WO | 03/082232 | 10/2003 |
| WO | 2005/065632 | 7/2005 |

OTHER PUBLICATIONS

Jurczk, Matthew F.; Floyd, Davis T. et al.; "Cationic Surfactants and Quaternary Derivatives for Hair and Skin Care" Cosmetic Science and Technology Series, vol. 21, 1999, pp. ISSN: 0887-6541.

* cited by examiner

*Primary Examiner* — Jyothsna Venkat
(74) *Attorney, Agent, or Firm* — Norris McLaughlin & Marcus, P.A.

(57) ABSTRACT

Conditioning and shine enhancing compositions dramatically and condition hair excellently in terms of combability, elasticity, smoothness and softness for keratin fibers especially human hair are disclosed. Particularly, the compositions disclosed comprise synthetic mica coated with metal oxide or oxides and having a volume particle size distribution of 1 to 750 µm at a concentration of 0.01 to 10% by weight, calculated to total composition, which gives hair shimmery shine.

18 Claims, No Drawings

COMPOSITION FOR KERATIN FIBRES

This is a divisional patent application of U.S. Ser. No. 11/938,345, which was filed on Nov. 12, 2007.

FIELD OF THE INVENTION

The present invention relates to conditioning and shine enhancing compositions for keratin fibres especially human hair. More specifically, the present invention relates to compositions comprising synthetic mica coated with metal oxide or metal oxides.

BACKGROUND OF THE INVENTION

Hair conditioning compositions have widely been used for improving primarily combability of hair and furthermore enhancing smoothness, elasticity and shine. Many type of conditioners have been found on the market varying from emulsions, which are generally rinsed off from hair after application and certain period of processing time, to low viscosity lotions used without rinsing off after application. Hair shine improvement has been one of the main areas of development. Hair shine is very much related to the surface structure of hair and this varies very much with the degree of damage either by environmental effects or chemical treatment of hair such as permanent shaping or oxidative colouring. Although consumers with healthy non-damaged hair are generally satisfied with hair shine, shine of damaged hair is usually found to be unsatisfactory. There have been studies aiming improving shine of especially damaged hair.

Conditioner either leave-in and rinse off types have been widely used in hair dressing area. In the last decade especially leave-in conditioning compositions have gained much attention starting from Europe and still increasingly growing in Asian markets.

Leave-in conditioning compositions are especially found appropriate by consumers as they can generally be applied at the sites where necessary and the processing time does not have to be predetermined and more importantly washing hair after certain processing time is not needed.

Shine is an important property of hair indicating its healthiness and cosmetically appealing look. Although shine enhancing preparations are widely available, there is still need for improvement.

Additionally, shine enhancing of hair together with other hair care benefits are increasingly been found as main product benefit. Among other products, products with two physically separated phases at zero share rate have recently been put onto market.

For example WO 02/060397 discloses dual phase conditioning and styling composition for heat styling hair. According to the document compositions comprise an oil phase comprising volatile oil and an aqueous alcoholic phase comprising styling polymer, an emulsifier and salt. The document does not address at all shine enhancing of hair and especially does not disclose any composition which may fall within the scope of the present invention.

EP 996 408 discloses dual phased compositions for make up cleansing wherein a polyvinylpyrrolidone copolymer is used as a demixing agent. The documents does not address at all hair care application of such composition.

SUMMARY OF THE INVENTION

The inventors of the present invention have surprisingly found out that compositions comprising synthetic mica coated with metal oxide or metal oxides improve hair shine dramatically and condition hair excellently in terms of combability, elasticity, smoothness and softness.

Accordingly one embodiment of the present invention relates to an aqueous composition comprising at least one cationic surfactant at a concentration of 0.01 to 10% by weight, and at least one colour effect pigment consisting of synthetic mica coated with metal oxide or oxides and having a volume particle size distribution in the range of 1 to 750 μm at a concentration of 0.01 to 10% by weight, calculated to total composition.

Another embodiment of the present invention relates to an aqueous composition comprising at least one silicone compound at a concentration of 0.01 to 10% by weight, and at least one colour effect pigment consisting of synthetic mica coated with metal oxide or oxides and having a volume particle size distribution in the range of 1 to 750 μm at a concentration of 0.01 to 10% by weight, calculated to total composition.

A further embodiment of the present invention relates to a water in oil emulsion composition comprising at least one volatile silicone oil and at least one water in oil emulsifier and an internal water phase comprising synthetic mica coated with metal oxide or oxides and having a volume particle size distribution in the range of 1 to 750 μm.

Yet another of the present invention comprises a two phase composition for hair comprising 5 to 50%, by weight oil phase, 50 to 95%, by weight water phase and 0.001 to 10% by weight, all values are calculated to total composition, synthetic mica coated with metal oxide or oxides and having a volume particle size distribution in the range of 1 to 750 μm, wherein oil and aqueous phases are optically separated at zero shear rate and becomes homogeneous upon shaking and returns again to optically separated two phases upon release of agitation.

DETAILED DESCRIPTION OF THE INVENTION

Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference. Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

Compositions of one embodiment of the present invention comprise at least one cationic surfactant at a concentration of 0.01 to 10%, preferably 0.05 to 7.5%, more preferably 0.1 to 5% by weight calculated to total composition.

As a rule any cationic surfactant is suitable for the compositions of the present invention. With the term cationic surfactant it is meant that the surfactant carries a cationic charge when used in the compositions. In other words, compounds having no cationic charge but when added into the compositions protonate and therewith become cationic are also included within the definition of cationic surfactant. An example to such may be stearyldimethylamine and PEG-2 Cocamine are as a compound not carrying a cationic charge but when used in a composition having acidic pH becomes cationic by protonation.

Preferably at least one cationic surfactant is selected from the compounds with the general formula

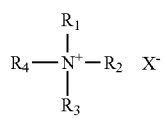

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and
$R_2$ is a hydrogen, saturated or unsaturated, branched or non-branched alkyl chain with 1-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4,
and $R_3$ and $R_4$ are independent from each other H or lower alkyl chain with 1 to 4 carbon atoms or ethoxy or propoxy group with number of ethoxy or propoxy groups varying in the range of 0 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, stearamidopropyldimethylamoonium chloride, dipalmitoyl dimonium chloride, distearyl dimethyl ammonium chloride, stearamidopropyl trimonuim chloride.

Further examples to the cationic surfactants are so called esterquats available on the market, for example, under the trade names "Schercoquat®", "Dehyquart® F30" and "Tetranyl®". Still further examples are so called amidoquats Again available on the market, for example, under the trade name "INCROQUAT$^a$ HO" or "OCS".

Compositions of the present embodiment can be in the form of a thin liquid, emulsion, thickened liquid or gel. In the case that the compositions are in the form of a thin liquid, it may be that metal oxide or oxides coated synthetic particles are precipitated or flocculated so that should be used after uniformly distributing the particles in the composition by agitation by for example shaking. In such a case it should also be possible to mix metal oxide or oxides coated synthetic mica particles prior to application onto keratin fibres with a composition comprising at least one cationic surfactant. Emulsion, thickened liquid and gel compositions are preferred within the meaning of the present embodiment.

Accordingly, another subject of the present embodiment is process for treating keratin fibres especially human hair wherein synthetic mica coated with metal oxide or oxides is added into the composition comprising at least one cationic surfactant prior to application onto hair.

Compositions of another embodiment of the present invention comprise at least one silicone compound at a concentration of 0.01 to 10%, preferably 0.05 to 7.5%, more preferably 0.1 to 5% by weight calculated to total composition.

Suitable silicone compounds are those water soluble or insoluble organosiloxane polymers having a linear or cyclic or branched or cross-linked structure, volatile or nonvolatile with variable molecular weight which are commercially largely available for conditioning keratin fibres especially human hair. Suitable polysiloxanes may be volatile or non volatile, substituted with linear or branched, saturated or unsaturated alkyl or alkoxy chain, or with an amine group or with an aromatic group such as phenyl.

Suitable polysiloxanes include dimethicone, dimethiconol, polydimethylsiloxane, DC fluid ranges from Dow Corning, cyclosiloxanes such as DC 245, arylated silicones such as phenyltrimethicone available from Dow Corning under trade name DC 556.

Further suitable silicones are aminated silicones with at least one primary, secondary tertiary, or quaternary amine group. Example to such compounds are amodimethicone commercially available from Dow Corning under the trade name DC 949 or polysilicone-9 commercially available from Kao Corporation, trimethylsilylamodimethicone commercially available under trade name Q2-8220 from Dow Corning.

The cationic polymers also include the quaternized products of graft polymers from organopolysiloxanes and polyethyl oxazolines described in EP-A 524 612 and EP-A 640 643.

Suitable non-limiting examples of polyoxyalkylenated silicones are those available from Goldschmidt under the trade name Abil, from Rhodia Chemie under the trade name Mirasil, from Dow Corning under trade names such as DC Fluid 190, DC 3225 C, Q2-5220, from Shin Etsu under trade name KF 351, from Wacker under trade name Belsil.

In case that a water insoluble or immiscible silicone is used the composition can be in form of two phases which should be shaken to homogeneity prior to application.

Compositions of the present embodiment can be in the form of a thin liquid, emulsion, thickened liquid and gel. In the case that the compositions are in the form of a thin liquid, it may be that metal oxide or oxides coated synthetic particles are precipitated so that should be used after uniformly distributing the particles in the composition by agitation for example by shaking prior to application. In such a case it should also be possible to mix metal oxide or oxides coated synthetic mica particles prior to application onto keratin fibres with a composition comprising at least one silicone compound. Emulsion, thickened liquid and gel compositions are preferred within the meaning of the present embodiment.

Accordingly, another subject of the present embodiment is process for treating keratin fibres especially human hair wherein synthetic mica coated with metal oxide or oxides is added into the composition comprising at least one silicone compound prior to application onto hair.

Another object of the present invention is the use of a water in oil emulsion composition comprising at least one volatile silicone oil and at least one water in oil emulsifier and an internal water phase comprising synthetic mica coated with metal oxide or oxides and having a volume particle size distribution in the range of 1 to 750 µm for conditioning hair.

Compositions of this embodiment of the present invention are preferably leave in compositions. It should be noted that rinsing off after application should not be seen as totally excluded from the scope. The most beneficial effects of the compositions of the present embodiment are observed in leave in application, i.e. when the compositions are not rinsed off from hair after application.

Still another subject of the present invention is a process for conditioning wet and/or freshly cleansed hair wherein a water in oil emulsion composition comprising at least one volatile silicone oil and at least one water in oil emulsifier and an internal water phase comprising synthetic mica coated with metal oxide or oxides and having a volume particle size distribution in the range of 1 to 750 µm is applied to hair and without rinsing off, hair is dried.

Still further object of the present invention is a process for conditioning dry hair wherein a water in oil emulsion composition comprising at least one volatile silicone oil and at least one water in oil emulsifier and an internal water phase comprising synthetic mica coated with metal oxide or oxides and having a volume particle size distribution in the range of 1 to 750 µm is applied to hair.

The compositions of the present embodiment comprise at least one volatile silicone oil. As a rule all silicone oils commercially available defined as volatile are suitable for the present invention. Preferred are those of cyclo organopolysiloxanes with the general formula

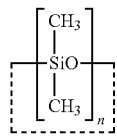

where n is a number between 3 and 7, which are available from Dow Corning with the trade name for example DC 245 which is cyclopentasiloxane where n=5.

Further volatile silicones suitable are known also from Dow Corning with the trade name DC 200 Fluid which includes a series of trisiloxanes with varying viscosities. Within the meaning of the present invention trisiloxanes with viscosity at 20° C. below or equal to 50 mPa·s are suitable. More preferred are trisiloxanes with a viscosity below or equal to 20 mPa·s, most preferred are those of with a viscosity below or equal to 5 mPa·s.

Concentration of one or more volatile silicone oil is in the range of 10 to 50%, preferably 15 to 40% and more preferably 20 to 30% by weight, calculated to total composition.

Compositions of the present invention comprise one or more water in oil emulsifier. Suitable ones are known in the textbooks as water in oil emulsifiers with HLB values generally below 10. Examples are mono or diglycerides with a fatty acyl chain length of 16 to 22 C atoms and silicone surfactants, especially ethoxylated and/or propoxylated dimethicone with number of ethoxy and/or propoxy groups in the range of 5 to 25. Preferred are ethoxylated and propoxylated silicone surfactants with number of ethoxy and propoxy groups each in the range of 10 to 20, more preferably 15 to 20. The most preferred emulsifiers are PEG/PPG 18/18 Dimethicone which is available from Dow Corning with the trade name DC 5225 C and PEG/PPG 20/15 Dimethicone available under trade name SF 1540 from GE silicones. Concentration of water in oil emulsifier is in the range of 0.1 to 5%, preferably 0.25 to 3%, more preferably 0.5 to 2.5% by weight, calculated to total composition.

Compositions of the present invention comprise in internal water phase synthetic mica coated with metal oxide or oxides having a volume particle size distribution in the range of 1 to 750 µm. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail. The content of the document is included herewith by reference.

Compositions of the present embodiment comprise preferably an inorganic salt such as sodium chloride, magnesium sulphate, magnesium chloride at a concentration of 0.1 to 3%, preferably 0.25 to 2% and more preferably 0.5 to 1.5% by weight calculated to total composition. Preferred are sodium chloride and magnesium sulphate.

Composition of the present embodiment can comprise one or more non-volatile oil(s) in the oil phase. Suitable ones are non-volatile silicones such as dimethicone or dimethiconol commercially available for example from Dow Corning, or arylated non volatile silicones such as phenyl trimethicone also available from Dow corning. Further suitable oils are natural oils such as olive oil, almond oil, avocado oil, ricinus oil, jojoba oil, coconut oil, palm oil, sesame oil, peanut oil, whale oil, sunflower oil, peach kernel oil, wheat germ oil, macadamia nut oil, night primrose oil, castor oil, or soya oil, lanolin and the derivatives thereof or their mixture, and mineral oil such as paraffin oil or petrolatum.

Further, compositions of the present embodiment can comprise fatty acid esters as oily substances such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

The above mentioned non-volatile oils can also be used in mixture with each other. Nonvolatile oils may be added into the compositions of the present invention at a concentration in the range of 0.01 to 5%, preferably 0.05 to 3%, more preferably 0.1 to 2% by weight, calculated to total composition.

Compositions of the present invention can comprise one or more fixing polymer(s) selected from anionic, cationic, amphoteric and nonionic ones or their mixtures. Although not limiting, one of the points in selecting fixing polymer is that the polymer should be soluble in the rest of the composition, preferably in water phase, without leaving undissolved rests.

Suitable anionic polymers are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/ crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof.

Suitable non-ionic polymers are polyvinylpyrrolidone, polyvinylpyrrolidone/vinylacetate copolymer and polyvinylpyrrolidone/vinylacetate/vinylpropionate copolymer. Preferred is polyvinylpyrrolidone/vinylacetate copolymer. In addition to these fixing polymers derivatives of natural polymers such as hydroxylethylcellulose may also be used alone or in combination with one of the fixing polymers mentioned above.

Suitable cationic polymers include Polyquaternium-4, Polyquaternium-11, Polyquaternium-16, Polyquaternium-18, Polyquaternium-24, Polyquaternium-28, Polyquaternium-46, polyvinylpyrrolidone/dimethylaminoethyl methacrylate, and cationically derivatized natural polymers. Preferred are Polyquaternium-4, Polyquaternium-11 and Polyquaternium-16.

Suitable amphoteric polymers are those available from the company National Starch under the trade name Amphomer such as Octylacrylamide/Acrylates/Butylaminoethyl methacrylate copolymer, those available under the trade name Diaformer (methacryloylethylbetaine/methacrylates copolymer). Preferred are the ones available under the trade name Amphomer.

As a fixing polymer silicone containing polymers either grafted or block copolymer are also useful. Suitable and the preferred one is Polysilicone-9.

Concentration of any of the fixing polymer or their mixtures is in the range of 0.1 to 15%, preferably 0.5 to 10%, more preferably 1 to 7.5% by weight calculated to total composition.

Yet another composition of the present invention comprises embodiments relating to compositions comprising optically separated two phases which becomes homogeneous upon shaking and returns again to optically separated two phases upon release of agitation. Compositions of the present embodiment returns to optically separated two phases upon release of agitation preferably within 24 hours, more preferably within 20 hours and most preferably within 10 hours. It should be noted that with the compositions of the present invention separated oil and aqueous phases are recognizable after 15 to 30 minutes of shaking. The above mentioned separation periods refer to the complete separation of the two phases i.e. returning to their original state.

Compositions of the present embodiment comprises oil phase at a concentration of 5 to 50%, preferably 10 to 40% more preferably 15 to 30% by weight calculated to total composition. Oil phase comprises 70 to 100%, preferably 80 to 100% and more preferably 90 to 100% by weight calculated to the content of oil phase at least one volatile oil. Suitable volatile oils are silicones such as dimethicone and cyclomethicone and mixtures thereof, and volatile hydrocarbons such as isododecane, isohexadecane and isoprafin. The most preferred are silicones and from those dimethicone and cylomethicone and mixtures thereof.

Suitable volatile dimethicones are the ones with a viscosity of less than 5 mm²/s. The most preferred are dimethicone with a viscosity of 1 mm²/s and 0.65 mm²/s which are available from Dow Corning with the trade name DC 200 Fluid.

Suitable volatile cyclomethicones are according to general formula

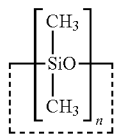

where n is a number between 3 and 7. Preferred are cyclopentasiloxanes known with the trade name for example Dow Corning 245.

Non-volatile silicones may also be incorporated into the compositions of the present embodiment at a low concentration, i.e. lower than 2%, preferably in the range of 0.01 to 1% by weight calculated to the content of oil phase. Suitable ones are arylated silicones such as phenyltrimethicone known with the trade name Dow Corning 556, and dimethicones and dimethiconol with higher viscosity available from Dow Corning under the trade name DC 200 fluid with higher viscosity values.

In addition, natural oils such as olive oil, almond oil, avocado oil, ricinus oil, jojoba oil, coconut oil, palm oil, sesame oil, peanut oil, whale oil, sunflower oil, peach kernel oil, wheat germ oil, macadamia nut oil, night primrose oil, castor oil, or soya oil or their mixture, and mineral oil such as paraffin oil or petrolatum may suitably be contained. Concentration of natural oils are below 2%, preferably in the range of 0.01 to 1.0% by weight calculated to the content of the oil phase. As a rule selected natural oil should be soluble in and/or miscible with the volatile oil used in the composition.

Further compositions of the present embodiment can comprise fatty acid esters as non-volatile oily compounds such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc. at the same concentration range as the natural oils.

Compositions of the present embodiment comprise aqueous phase at a concentration of 50 to 95%, preferably 60 to 90% more preferably 70 to 85% by weight calculated to total composition.

Synthetic mica is preferably added as dispersed in water phase. It has been observed that the synthetic mica particles coated with metal oxide or oxides migrate to the water and oil interphase. This does not effect the performance of the composition as shaking is required prior to application. This phenomenon should also not be seen as the formation of the third phase as particles migrated to the oil-water interphase are still dispersed in water and contained in the water phase.

Preferably, compositions of the present embodiment comprise at least one hair conditioning compound in the aqueous. Suitable hair conditioning compounds are those water soluble and/or water miscible compounds such as cationic surfactants, cationic polymers, polyols and natural plant extracts. It should be noted that cationic polymers can also be used as hair fixing agent.

One or more cationic surfactant(s) as hair conditioners is (are) contained in aqueous phase of the compositions of the present invention at a concentration of 0.01 to 2%, preferably 0.05 to 1.5%, more preferably 0.1 to 1.0% by weight calculated to the content of the aqueous phase. Suitable cationic surfactants are according to the general formula

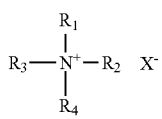

where $R_1$ is a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

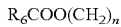

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

Where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, ethoxy or propoxy group with number of ethoxy or propoxy groups varying in the range of 0 to 4 and X is chloride, bromide or methosulfate.

Suitable cationic surfactants are particularly cetyl trimethly ammonium chloride, steartrimonium chloride, behentrimoinium chloride, stearamidopropyl trimonuim chloride, behenamidopropylethyldimonium ethosulfate, behenamidopropyltrimonium methosulfate, cocamidopropyltrimonium chloride, cocotrimonim chloride, palmitamidopropyltrimonum chloride, dipalmitoyltrimonium chloride, di-C12-C15 alkyldimoniumchloride, distearyldimonium chloride, dipalmitoylethylhydroxyethylmonium chloride, dioleoylethyl dimethyl ammonium methosulfate, dioleoylethyl hydroxyethylmonium methosulfate, dilinolamidopropyldimonium chloride, dioleylethyl hydroxyethylmonium chloride and dipalmitoylethyldimonium chloride.

One or more polyol(s) as hair conditioners is (are) comprised in the aqueous phase of the compositions of the present invention at a concentration of 0.01 to 10%, preferably 0.05 to 7.5%, 0.1 to 5% by weight calculated to total of aqueous phase.

Suitable ones are panthenol, glycerol, polyethylene glycols with molecular weight 200 to 20,000.

Natural plant extracts may as well form part of the compositions of the present invention. Natural extracts should be included into the aqueous phase of the compositions. Suitable aqueous (e.g. steam-distilled) alcoholic or hydro-alcoholic plant extracts known per se are in particular extracts from leaves, fruits, blossoms, roots, rinds or stems of almond, aloe, pineapple, artichoke, arnica, avocado, valerian, henbane, birch, stinging nettle, echinacea, ivy, wild angelica, gentian, ferns, pine needles, silver weed, ginseng, broom, bamboo, green tea, oat, rose hip, hamamelis, hay flowers, elderberry, hop, coltsfoot, currants, chamomile, carrots, chestnuts, clover, burr root, coconut, coconut, mango, peach, lemon, cornflower, wheat, apricot, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Preferably, compositions of the present embodiment comprise one or more hair fixing polymers in aqueous phase at a concentration of 0.1 to 20%, preferably 0.5 to 15%, more preferably 0.5 to 10% by weight calculated to the content of aqueous phase.

Suitable polymers are non-ionic, cationic, amphoteric and anionic polymers. One of the important point in selecting fixing polymer is that the polymer should not thicken the aqueous phase. In other words the viscosity of the aqueous phase should remain low i.e. below 100 mPa·s, preferably 50 mPa·s measured at 20° C.

Suitable non-ionic polymers are polyvinylpyrrolidone, polyvinylpyrrolidone/vinylacetate copolymer and polyvinylpyrrolidone/vinylacetate/vinylpropionate copolymer. Preferred is polyvinylpyrrolidone/vinylacetate copolymer. In addition to these fixing polymers derivatives of natural polymers such as hydroxylethylcellulose may also be used in combination with one of the fixing polymers mentioned above.

Suitable cationic polymers include Polyquaternium-4, Polyquaternium-11, Polyquaternium-16, Polyquaternium-18, Polyquaternium-24, Polyquaternium-28, Polyquaternium-46, polyvinylpyrrolidone/dimethylaminoethyl methacrylate, and cationically derivatized natural polymers. Preferred are Polyquaternium-4, Polyquaternium-11 and Polyquaternium-16.

Suitable amphoteric polymers are those available from the company National Starch under the trade name Amphomer such as Octylacrylamide/Acrylates/Butylaminoethyl methacrylate copolymer, those available under the trade name Diaformer (methacryloylethylbetaine/methacrylates copolymer). Preferred are the ones available under the trade name Amphomer.

As a fixing polymer silicone containing polymers either grafted or block copolymer are also useful. Suitable and the preferred one is Polysilicone-9.

Aqueous phase of the compositions of the present embodiment comprise 5 to 40%, preferably 10 to 35%, more preferably 15 to 30% by weight calculate to the content of aqueous phase at least one water miscible organic solvent. With the term "water miscible" it is meant that the organic solvent is miscible with water at any ratio. Suitable ones are $C_2$-$C_4$ monohydric alcohols such as ethanol, propanol, isopropanol, butanol and isobutanol, benzyl alcohol and benzyloxyethanol and their mixtures. Most preferred are ethanol and isopropanol.

The pH of the aqueous phase varies from 3 to 7, particularly 4.5 to 6. For adjusting the pH of the said conditioner compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, pyruvic acid, salicylic acid or acetic acid or inorganic acids such as hydrochloric acid, phosphoric acid, sulphuric acid, nitric acid. The pH of the conditioner composition can also be adjusted to the required pH by using alkaline solution such as sodium hydroxide, potassium hydroxide, ammonium hydroxide or their salts with those acids mentioned above.

The aqueous and oil phases of the compositions of the present invention may be coloured. The dyestuff suitable for product colouring purposes are all useful for this purpose. It should be noted that for colouring aqueous phase water soluble dyes should be used and for colouring oil phase oil soluble dyes are suitable. The nature of the dyestuff is actually not important but preferred are non substantive dyes, i.e. not remaining on hair after washing with water or shampooing.

Fragrance, chelating agent, preservatives and other conventional cosmetic ingredients can be included at their usual concentrations either into the oil or aqueous phases depending on their solubility.

Composition of the present invention are leave-in composition, i.e. not rinsed off from hair after application. Accordingly, in a process compositions of the present invention are applied to the shampooed and/or wetted hair and hair is dried. Compositions of the present invention are also applied onto dry hair. It is possible to apply compositions of the present invention as a lotion and also from a bottle equipped with a pump spray. Preferred application is spraying onto hair.

The compositions of the present invention may be transparent or turbid. Turbidity may be caused by the presence of synthetic mica particles or any other ingredient.

With the term thickened liquid, it is meant that the compositions comprise additionally a thickening agent.

With the term gel it is meant that the compositions comprise additionally a gelling agent and the gelling agent is a polymer forming a shear thinning gel.

The thickening agents include any polymer either natural or synthetic thickening aqueous composition. Examples are cellulose and its derivatives such as hydroxyethylcellulose, guar and its derivatives such as hydroxypropyl guar. In the selection of the thickening gels compatibility with cationic surfactant should be carefully examined.

The gelling agents include polymers either synthetic or natural forming shear thinning compositions. Examples to the natural polymers are xanthan gum and its derivatives. Synthetic shear thinning polymers may be those of acrylate polymers wherein compatibility with cationic surfactant should carefully be examined prior to use.

Concentration of the thickening and/or gelling agents should be in the range of 0.05 to 5%, preferably 0.1 to 2.5% by weight calculated to total content. It should also be noted that gelling and thickening polymers can be used together.

Another preferred form is oil in water (O/W) emulsion. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 20%, preferably 0.5 to 15% and more preferably 1 to 10% by weight calculated to total composition.

Emulsions should also comprise at least one emulsifier. It should be noted that quaternary ammonium compounds with single alkyl chain mentioned above are preferred as emulsifiers as well.

In addition to the cationic surfactants with single alkyl chain, additional emulsifier can be incorporated into the compositions. These additional emulsifiers are surface active substances such as non-ionic, amphoteric or zwitterionic and anionic compounds. Because of the compatibility issues of the anionic surfactants and cationic surfactants mentioned above, anionic surfactants are less suitable and therefore their compatibility should carefully be examined. Otherwise, the compositions of the present invention preferably should substantially be free of anionic surfactants. Preferred emulsifiers are cationic, non-ionic, amphoteric or zwitterionic surfactants. The most preferred additional emulsifiers are non-ionic surfactants.

Suitable non-ionic surfactants are alkyl polyglucosides of the general formula

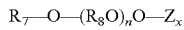

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant component as emulsifier, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Additional emulsifier content of the compositions according to present invention is in the range of 0.05 to 10%, preferably 0.1 to 7.5% and more preferably 0.25 to 5% by weight calculated to total composition.

Compositions of the present invention can comprise additional hair conditioning compounds such as oils, cationic polymers, non-ionic substances. Oils as conditioners according to the present invention are selected from silicone oils either volatile or non-volatile, natural and synthetic oils. Among silicone oils those can be added to the compositions include dimethicone, dimethiconol, polydimethylsiloxane, DC fluid ranges from Dow Corning, cyclosiloxanes such as DC 245, arylated silicones such as phenyltrimethicone available from Dow Corning under trade name DC 556. Synthetic oils include mineral oil such as paraffin oil and petrolatum.

Natural oils suitable are such as olive oil, almond oil, avocado oil, weizenkeim oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are as well suitable for the composition of the present invention. Those are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

$R_9CO(OCH_2CH_2)_nOH$

$R_9CO(OCH_2CH_2)_nOOCR_{10}$ where $R_9$ and $R_{10}$ are independent from each other saturated, unsaturated or branched or non-branched alkyl chain with 7 to 21 C atoms and n is typically 2-100.

Typical concentration range for any of the additional conditioners mentioned above other than cationic conditioning compounds can be in the range of 0.01 to 15% by weight, preferably 0.05-10% by weight, more preferably 0.1-5% by weight calculated to the total composition.

Composition of the present invention comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The cationic polymers also include the quaternized products of graft polymers from organopolysiloxanes and polyethyl oxazolines described in EP-A 524 612 and EP-A 640 643.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", $4^{th}$ Ed.

The compositions may contain organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvents in the composition should not exceed 5% by weight. It should be noted that penetration enhancers are useful for both cleansing and after shampoo conditioning preparations. It is obvious that the concentration in the cleansing compositions is usually lower than in the conditioning preparations.

Compositions of the present invention can comprise UV filters either for stabilization of the product colour or for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxybenzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition.

The compositions of the present invention can comprise hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are those with 10 to 24 carbon atoms and especially with 16 to 24 carbon atoms.

Sterols, especially the phytosterols, are as well preferred hair restructuring agents as disclosed in the above mentioned German patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably in the range of 0.01 to 0.5% by weight calculated to the total weight of the composition. It should be noted without limiting the use of those ingredients the effect of those hair restructuring ingredients is especially elevated when used in combination with penetration enhancers.

The pH of the compositions according to the invention is in the range of 2 to 7, preferably 3 to 6, more preferably 3 to 5. For adjusting the pH of the said compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be chosen in a way that composition reaches the desired pH value as given above. Typically concentration for acids can be 0.01-3% by weight, preferably 0.05-2% by weight, more preferably 0.05-1.5% by weight calculated to the total composition. The pH of the composition can also be adjusted to the required pH by using alkaline solution such as sodium hydroxide, ammonium hydroxide, potassium hydroxide or their salts with those acids mentioned above in the case that at the selected acid concentration pH of the composition is lower than that of the aimed value.

Furthermore compositions of the present invention can comprise all substances customarily found in such preparations. Examples of such substances are complexing agents, dyestuffs preferably non-substantive for colouring composition, preservatives, fragrances, etc.

Compositions of certain embodiments of the present invention are used as a rinse off conditioners and usually used after cleansing hair. On the other hand usage without previous cleansing should not be excluded. Accordingly, process for conditioning keratin fibres especially human hair, especially enhancing shine consists of washing hair, preferably with a cleansing composition and then applying a composition comprising at least one cationic surfactant at a concentration of 0.01 to 10% by weight, and at least one colour effect pigment consisting of synthetic mica coated with metal oxide or oxides and having a particle size distribution of 1 to 750 μm at a concentration of 0.01 to 10% by weight, calculated to total composition, onto hair and after processing for 30 sec to 30 min, preferably 1 min to 15 min and more preferably 3 minute to 10 min at ambient temperature or at a temperature not exceeding 40° C., rinsed off.

Following examples are to illustrate the invention but not to limit.

Example 1

|  | % by weight |
| --- | --- |
| Cetrimonium chloride | 2.0 |
| Synthetic fluorphologopite* | 1.0 |
| Citric acid/Sodium hydroxide | q.s. to pH 4.0 |
| Fragrance | 0.2 |
| Solubilizer** | 0.2 |
| Water | to 100 |

*Synthetic fluorphologopite used is commercially available from Sun Chemical Corporation under the trade name SunShine Glitter White with a particle size distribution in the range of 20 to 95 μm.
**any solubilizer may be used preferred are those ethoxylated ricinus oil, preferably hydrogenated ricinus oil. In the above example and other examples below where necessary PEG-60 hydrogenated ricinus oil is used preferably at a weight ratio of fragrance to solubilizer 1:1.

The above composition was prepared by combining cetrimonium chloride (a commercially available 25% by weight solution was used) with remaining water. Afterwards fragrance and solubilizer was combined, solubilizer was heated slightly to melt before, and added to the solution of cetrimonium chloride. Finally synthetic fluorphologopite was dispersed and pH was adjusted to 4.0.

The above composition was tested in a half side test with 10 consumers having shoulder length hair. Before application of the above composition, hair was washed with a commercially available shampoo. Afterwards to the half side 5 g of the above composition was applied and the other half was left untreated. After processing time of 5 min at ambient temperature the composition was rinsed off from hair. The hair was towel dried and dried with a hair drier. The hair was combable and had excellent shimmery shine. The composition was shaken to homogeneity prior to application. Interestingly spraying is also possible application way.

Example 2

|  | % by weight |
| --- | --- |
| Cetearyl alcohol | 10.0 |
| Behentrimonium chloride | 2.0 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Glitter White with a particle size distribution in the range of 20 to 95 μm.

Above composition was prepared first by emulsifying cetearyl alcohol and behentrimonium chloride at a temperature of approximately 75° C. in part of water.

Afterwards the composition was cooled down and remaining water was added which was followed by addition of fragrance and Synthetic fluorphologopite pre-dispersed in a small portion of water. Finally pH was adjusted.

For comparative purposes the same composition but not comprising Synthetic fluorphologopite was also produced.

The above composition was tested in a half side test against the comparative composition without Synthetic fluorphologopite in the same way as in Example 1 with 10 consumers having shoulder length hair. Comments from the consumer were both side feels soft and combable but the side treated with the inventive composition has significantly more shimmery shine than the side treated with the comparative composition. The preference was 10/0.

Example 3

| | % by weight |
|---|---|
| Cetearyl alcohol | 10 |
| Behentrimonium chloride | 2.0 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Ultra Glitter White with a particle size distribution in the range of 95 to 730 µm.

The composition was prepared in the similar way as in Example 2.

In a half side test similar results were obtained as in the Example 2.

Similar results were observed with the compositions below.

Example 4

| | % by weight |
|---|---|
| Cetearyl alcohol | 10 |
| Behentrimonium chloride | 2.0 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Super Glitter White with a particle size distribution in the range of 40 to 250 µm.

Example 5

| | % by weight |
|---|---|
| Behentrimonium chloride | 2.0 |
| Synthetic fluorphologopite* | 1.0 |
| Hydroxyethylcellulose | 1.0 |
| Citric acid/Sodium hydroxide | q.s. to pH 4.0 |
| Fragrance | 0.4 |
| Solubilizer as in Example 1 | 0.4 |
| Water | to 100 |

*Synthetic fluorphologopite used is commercially available from Sun Chemical Corporation under the trade name SunShine Glitter White with a particle size distribution in the range of 20 to 95 µm.

Example 6

| | % by weight |
|---|---|
| Behentrimonium chloride | 1.5 |
| Synthetic fluorphologopite* | 1.0 |
| Polyquaternium-10 | 0.7 |
| Hydroxyethylcellulose | 0.5 |
| Citric acid/Sodium hydroxide | q.s. to pH 3.5 |
| Fragrance | 0.4 |
| Solubilizer as in Example 1 | 0.4 |
| Water | to 100 |

*Synthetic fluorphologopite used is commercially available from Sun Chemical Corporation under the trade name SunShine Glitter White with a particle size distribution in the range of 20 to 95 µm.

Example 7

| | % by weight |
|---|---|
| Behentrimonium chloride | 1.5 |
| Synthetic fluorphologopite* | 1.0 |
| Polyquaternium 37 | 0.5 |
| Citric acid/Sodium hydroxide | q.s. to pH 4.5 |
| Fragrance | 0.4 |
| Solubilizer as in Example 1 | 0.4 |
| Water | to 100 |

*Synthetic fluorphologopite used is commercially available from Sun Chemical Corporation under the trade name SunShine Glitter White with a particle size distribution in the range of 20 to 95 µm.

Example 8

| | % by weight |
|---|---|
| Behentrimonium chloride | 1.5 |
| Synthetic fluorphologopite* | 1.0 |
| Dimethicone | 0.5 |
| Hydroxypropyl guar | 0.8 |
| Citric acid/Sodium hydroxide | q.s. to pH 4.5 |
| Fragrance | 0.4 |
| Solubilizer as in Example 1 | 0.4 |
| Water | to 100 |

*Synthetic fluorphologopite used is commercially available from Sun Chemical Corporation under the trade name SunShine Glitter White with a particle size distribution in the range of 20 to 95 µm.

Example 9

| | % by weight |
|---|---|
| Dimethicone | 2.0 |
| Synthetic fluorphologopite* | 1.0 |
| Citric acid/Sodium hydroxide | q.s. to pH 4.0 |
| Fragrance | 0.2 |
| Water | to 100 |

*Synthetic fluorphologopite used is commercially available from Sun Chemical Corporation under the trade name SunShine Glitter White with a volume particle size distribution in the range of 20 to 95 µm.

The above composition was prepared by dispersing dimethicone and synthetic fluorphologopite in water and finally pH was adjusted to 4.

The above composition was tested in a half side test with 10 consumers having shoulder length hair. Before application of the above composition, hair was washed with a commercially available shampoo. Afterwards to the half side 5 g of the above composition was applied and the other half was left untreated. After processing time of 5 min at ambient temperature the composition was rinsed off from hair. The hair was towel dried and dried with a hair drier. The hair was combable and had excellent shimmery shine. Prior to application composition was shaken to homogeneity.

Example 10

|  | % by weight |
| --- | --- |
| Dimethiconol | 1.0 |
| Behentrimonium chloride | 2.0 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Glitter White with a volume particle size distribution in the range of 20 to 95 μm.

Above composition was prepared first by dissolving behentrimonium chloride in water with heat and subsequent dispersion of dimethiconol, synthetic fluorphologopite and fragrance therein after cooling. Finally pH was adjusted to 4.0.

For comparative purposes the same composition but not comprising Synthetic fluorphologopite was also produced.

The above composition was tested in a half side test against the comparative composition without Synthetic fluorphologopite in the same way as in Example 1 with 10 consumers having shoulder length hair. Comments from the consumer were both side feels soft and combable but the side treated with the inventive composition has significantly more shimmery shine than the side treated with the comparative composition. The preference was 10/0. Prior to application composition was shaken to homogeneity.

Example 11

|  | % by weight |
| --- | --- |
| Cetearyl alcohol | 10 |
| Behentrimonium chloride | 2.0 |
| Dimethicone | 1.0 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Ultra Glitter White with a volume particle size distribution in the range of 95 to 730 μm.

The composition was prepared in the similar way as in Example 10.

In a half side test similar results were obtained as in the Example 10.

Similar results were observed with the compositions of Examples 12-15 below.

Example 12

|  | % by weight |
| --- | --- |
| Cetearyl alcohol | 10 |
| Behentrimonium chloride | 1.0 |
| Amodimethicone | 0.8 |
| Synthetic fluorphologopite* | 1.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Super Glitter White with a volume particle size distribution in the range of 40 to 250 μm.

Example 13

|  | % by weight |
| --- | --- |
| Cetearyl alcohol | 10.0 |
| Ceteareth-20 | 2.0 |
| Synthetic fluorphologopite* | 1.0 |
| Dimethiconol | 2.0 |
| Citric acid/Sodium hydroxide | q.s. to pH 4.0 |
| Fragrance | 0.4 |
| Water | to 100 |

*Synthetic fluorphologopite used is commercially available from Sun Chemical Corporation under the trade name SunShine Glitter White with a volume particle size distribution in the range of 20 to 95 μm.

Example 14

|  | % by weight |
| --- | --- |
| Cetearyl alcohol | 10.0 |
| Behentrimonium chloride | 1.5 |
| Synthetic fluorphologopite* | 1.0 |
| Polyquaternium-10 | 0.7 |
| Dimethicone | 3.0 |
| Citric acid/Sodium hydroxide | q.s. to pH 3.5 |
| Fragrance | 0.4 |
| Solubilizer as in Example 1 | 0.4 |
| Water | to 100 |

*Synthetic fluorphologopite used is commercially available from Sun Chemical Corporation under the trade name SunShine Glitter White with a volume particle size distribution in the range of 20 to 95 μm.

Example 15

|  | % by weight |
| --- | --- |
| Behentrimonium chloride | 1.5 |
| Synthetic fluorphologopite* | 1.0 |
| Polyquaternium 37 | 1.5 |
| Dimethiconol | 2.0 |
| Citric acid/Sodium hydroxide | q.s. to pH 4.5 |
| Fragrance | 0.4 |
| Water | to 100 |

*Synthetic fluorphologopite used is commercially available from Sun Chemical Corporation under the trade name SunShine Glitter White with a volume particle size distribution in the range of 20 to 95 μm.

Example 16

|  | % by weight |
| --- | --- |
| Cyclopentasiloxane | 25 |
| PEG/PPG - 18/18 Dimethicone* | 1.4 |
| Synthetic fluorphologopite** | 0.5 |
| Sodium chloride | 1.1 |
| Fragrance, preservative, dyestuff | q.s |
| Water | q.s. to 100 |

*used as a raw material DC 5225 C and therefore minor amounts of other cyclosiloxanes are also present.
**Synthetic fluorphologopite used is commercially available from Sun Chemical Corporation under the trade name SunShine Glitter White with a particle size distribution in the range of 20 to 95 µm.

Above composition was prepared by dispersing PEG/PPG-18/18 Dimethicone in cyclopentasiloxanes which was combined with water containing dispersed Synthetic fluorphologopite and dissolved sodium chloride, dyestuff and preservative under agitation and subsequently homogenised with Ultrathorax at 9000 rpm.

The above composition used on dry and wet hair either wetted or cleansed and towel dried and it was observed that hair gained excellent shine, smoothness and elasticity. Furthermore, it was found that spreading on hair was very easy.

Example 17

|  | % by weight |
| --- | --- |
| Cyclopentasiloxane | 15 |
| Trisiloxane * | 10 |
| PEG/PPG - 20/15 Dimethicone** | 1.4 |
| Synthetic fluorphologopite*** | 0.5 |
| Magnesium chloride | 1.0 |
| Fragrance, preservative | q.s |
| Water | q.s. to 100 |

* DC 200 Fluid with a viscosity of 1 cst
**used as a raw material SF 1540
***Synthetic fluorphologopite used is commercially available from Sun Chemical Corporation under the trade name SunShine Glitter White with a particle size distribution in the range of 20 to 95 µm.

The composition was prepared in a similar way as in example 16.

Similar effects were observed when used on dry and wet hair as in example 16.

Example 18

|  | % by weight |
| --- | --- |
| Cyclopentasiloxane | 15 |
| Trisiloxane * | 10 |
| PEG/PPG - 18/18 Dimethicone** | 1.4 |
| Synthetic fluorphologopite*** | 0.4 |
| VP/VA copolymer | 1.5 |
| Magnesium sulphate | 0.9 |
| Fragrance, preservative, dyestuff | q.s |
| Water | q.s. to 100 |

* DC 200 Fluid with a viscosity of 1 cst
**used as a raw material DC 5225 C and therefore minor amounts of other cyclosiloxanes are also present.
***Synthetic fluorphologopite used is commercially available from Sun Chemical Corporation under the trade name SunShine Glitter White with a particle size distribution in the range of 20 to 95 µm.

The composition was prepared in a similar was as in example 16. The VP/VA polymer was dissolved in water.

Similar effects were observed when used on dry and wet hair as in Example 16. Additionally hair treated with the above composition had excellent body and volume.

Example 19

|  | % by weight |
| --- | --- |
| Trisiloxane * | 24.5 |
| Isopropyl palmitate | 0.5 |
| Octylmethoxycinnamate | 0.2 |
| PEG/PPG - 18/18 Dimethicone** | 1.4 |
| Synthetic fluorphologopite*** | 0.4 |
| Polyquaternium 11 | 1.5 |
| Magnesium sulphate | 0.9 |
| Fragrance, preservative, dyestuff | q.s |
| Water | q.s. to 100 |

* DC 200 Fluid with a viscosity of 1 cst
**used as a raw material DC 5225 C and therefore minor amounts of other cyclosiloxanes are also present.
***Synthetic fluorphologopite used is commercially available from Sun Chemical Corporation under the trade name SunShine Glitter White with a particle size distribution in the range of 20 to 95 µm.

The composition was prepared in a similar was as in example 16. The Polyqauternium-11 was dissolved in water and Isopropyl palmitate and UV filter was added into oil phase.

Similar effects were observed when used on dry and wet hair as in Example 18.

Example 20

|  | % by weight |
| --- | --- |
| Trisiloxane * | 24.5 |
| Isopropyl stearate | 0.3 |
| Polysilicone-15 | 0.2 |
| Polysilicone-9 | 0.5 |
| PEG/PPG - 18/18 Dimethicone** | 1.5 |
| Synthetic fluorphologopite*** | 0.6 |
| Polyquaternium 11 | 1.5 |
| Ethanol | 3.0 |
| Sodium chloride | 1.2 |
| Fragrance, preservative, dyestuff | q.s |
| Water | q.s. to 100 |

* DC 200 Fluid with a viscosity of 1 cst
**used as a raw material DC 5225 C and therefore minor amounts of other cyclosiloxanes are also present.
***Synthetic fluorphologopite used is commercially available from Sun Chemical Corporation under the trade name SunShine Glitter White with a particle size distribution in the range of 20 to 95 µm.

The above composition was prepared in a similar way as Example 16. Polysilicone 9 is added as 30% by weight ethanolic solution into water phase. UV filter polysilicone 15 was added into oil phase.

Example 21

|  | % by weight |
| --- | --- |
| Trisiloxane * | 15.5 |
| Cyclopentasiloxane | 11.0 |
| Phenyltrimethicone | 0.3 |

-continued

| | % by weight |
|---|---|
| Polysilicone-15 | 0.2 |
| PEG/PPG - 18/18 Dimethicone** | 1.5 |
| Synthetic fluorphologopite*** | 0.6 |
| Acrylates/butylacrylamide copolymer | 1.5 |
| Ethanol | 3.0 |
| Benzophenone-4 | 0.3 |
| Sodium chloride | 0.9 |
| Fragrance, preservative, dyestuff | q.s |
| Water | q.s. to 100 |

* DC 200 Fluid with a viscosity of 1 cst
**used as a raw material DC 5225 C and therefore minor amounts of other cyclosiloxanes are also present.
***Synthetic fluorphologopite used is commercially available from Sun Chemical Corporation under the trade name SunShine Glitter White with a particle size distribution in the range of 20 to 95 μm.

Example 22

| | % by weight |
|---|---|
| Trisiloxane * | 15.5 |
| Cyclopentasiloxane | 11.0 |
| Phenyltrimethicone | 0.3 |
| Polysilicone-15 | 0.2 |
| PEG/PPG - 20/15 Dimethicone** | 1.5 |
| Synthetic fluorphologopite*** | 0.6 |
| Ethanol | 3.0 |
| Cetrimonium chloride | 0.5 |
| Sodium chloride | 0.9 |
| Fragrance, preservative, dyestuff | q.s |
| Water | q.s. to 100 |

* DC 200 Fluid with a viscosity of 1 cst
**used as a raw material SF 1540.
***Synthetic fluorphologopite used is commercially available from Sun Chemical Corporation under the trade name SunShine Glitter White with a particle size distribution in the range of 20 to 95 μm.

Example 23

| | % by weight |
|---|---|
| Oil phase | |
| Trisiloxane* | 99.8 |
| Fragrance | 0.2 |
| Aqueous phase | |
| Synthetic fluorphologopite** | 0.5 |
| Citric acid/Ammonium hydroxide | q.s. to pH 6.0 |
| Water | to 100 |

*DC 200 Fluid with a viscosity of 1 cst
**Synthetic fluorphologopite used is commercially available from Sun Chemical Corporation under the trade name SunShine Glitter White with a particle size distribution in the range of 20 to 95 μm.

The above composition is used at a concentration of oil phase 20% by weight and aqueous phase 80% by weight, calculated to total composition.

For the comparative purposes the same composition without Synthetic fluorphologopite was also prepared.

The two compositions were compared in a half side test with 10 female volunteers and it was observed that the side treated with inventive composition was significantly more shiny, has better elasticity and felt smoother upon touching. Preference was 9/1, wherein in 1 case there was no difference seen. The composition was applied form a bottle with a spraying device after shaking to homogeneity.

Example 24

| | % by weight |
|---|---|
| Oil phase | |
| Trisiloxane* | 69.4 |
| Cyclopentasiloxane | 30.0 |
| Isopropyl myristate | 0.3 |
| Ethylhexylmethoxycinnamate | 0.1 |
| Fragrance | 0.2 |
| Aqueous phase | |
| Polyqauternium-11 | 0.5 |
| Synthetic fluorphologopite** | 0.5 |
| Steartrimoniumchloride | 0.15 |
| Ethanol | 20.0 |
| Lactic acid/Ammonium hydroxide | q.s. to pH 6.0 |
| Water | to 100 |

*DC 200 Fluid with a viscosity of 1 cst
**Synthetic fluorphologopite used is commercially available from Sun Chemical Corporation under the trade name SunShine Glitter White with a particle size distribution in the range of 20 to 95 μm.

Similar effects were observed when used on hair as in Example 23.

Example 25

| | % by weight |
|---|---|
| Oil phase | |
| Cyclopentasiloxane | 99.5 |
| Dimethicone 350 cp | 0.3 |
| Fragrance | 0.2 |
| Aqueous phase | |
| VP/VA copolymer | 0.5 |
| Synthetic fluorphologopite* | 0.3 |
| Ethanol | 20.0 |
| Lactic acid/Ammonium hydroxide | q.s. to pH 6.0 |
| Water | to 100 |

*Synthetic fluorphologopite used is commercially available from Sun Chemical Corporation under the trade name SunShine Glitter White with a particle size distribution in the range of 20 to 95 μm.

Similar effects were observed when used on hair as in Example 23.

Example 26

| | % by weight |
|---|---|
| Oil phase | |
| Trisiloxane* | 99.5 |
| Dimethicone 350 cp | 0.3 |
| Fragrance | 0.2 |
| Aqueous phase | |
| VP/VA copolymer | 0.5 |
| Synthetic fluorphologopite** | 0.3 |
| Ethanol | 20.0 |
| Benzophenone-4 | 0.2 |

-continued

| | % by weight |
|---|---|
| Citric acid/Sodium hydroxide | q.s. to pH 6.0 |
| Water | to 100 |

*DC 200 Fluid with a viscosity of 1 cst
**Synthetic fluorphologopite used is commercially available from Sun Chemical Corporation under the trade name SunShine Glitter White with a particle size distribution in the range of 20 to 95 μm.

Similar effects were observed when used on hair as in Example 23.

Example 27

| | % by weight |
|---|---|
| Oil phase | |
| Trisiloxane* | 99.7 |
| Almond oil | 0.1 |
| Fragrance | 0.2 |
| Aqueous phase | |
| Polyquaternium 16 | 0.5 |
| Cetrimonium chloride | 0.5 |
| Synthetic fluorphologopite** | 0.3 |
| Ethanol | 15.0 |
| Benzophenone-4 | 0.2 |
| Citric acid/Sodium hydroxide | q.s. to pH 6.0 |
| Water | to 100 |

*DC 200 Fluid with a viscosity of 0.65 cst
**Synthetic fluorphologopite used is commercially available from Sun Chemical Corporation under the trade name SunShine Glitter White with a particle size distribution in the range of 20 to 95 μm.

Similar effects were observed when used on hair as in Example 23.

Example 28

| | % by weight |
|---|---|
| Oil phase | |
| Dimethicone 1 cst | 99.6 |
| Benzophenone-3 | 0.2 |
| Fragrance | 0.2 |
| Aqueous phase | |
| VP/VA copolymer | 3.0 |
| Polysilicone-9 | 0.5 |
| Cetrimonium chloride | 0.15 |
| Dioleylethyl hydroxyethylmonium chloride | 0.15 |
| Synthetic fluorphologopite | 0.6 |
| Benzophenone-4 | 0.10 |
| Ethanol | 25.0 |
| Lactic acid/Ammonium hydroxide | q.s. to pH 7.0 |
| Dyestuff CI 19140 and CI 42053 | q.s. |
| Water | to 100 |

**Synthetic fluorphologopite used is commercially available from Sun Chemical Corporation under the trade name SunShine Glitter White with a particle size distribution in the range of 20 to 95 μm.

Similar effects were observed when used on hair as in Example 23.

The invention claimed is:

1. A method for increasing shine of hair, the method comprising:
preparing an aqueous hair conditioning composition comprising at least one cationic surfactant at a concentration of 0.01 to 10% by weight, and color effect pigment consisting of synthetic fluorphologopite and having a volume particle size distribution of 1 to 750 μm at a concentration of 0.01 to 10% by weight, calculated to total composition, and
increasing the shine of hair by applying the conditioning composition to the hair, leaving the conditioning composition on the hair for a processing time, and rinsing the conditioning composition from the hair, wherein the processing time is at least 30 second and no more than 30 minutes.

2. A method for increasing shine of hair, the method comprising:
preparing an aqueous hair conditioning composition comprising at least one silicone compound at a concentration of 0.01 to 10% by weight, and color effect pigment consisting of synthetic fluorphologopite and having a volume particle size distribution of 1 to 750 μm an at a concentration of 0.01 to 10% by weight, calculated to total composition, and
increasing the shine of hair by applying the conditioning composition to the hair, leaving the conditioning composition on the hair for a processing time, and rinsing the conditioning composition off the hair, wherein the processing time is at least 30 second and no more than 30 minutes.

3. The method according to claim 1, further comprising the step of:
washing the hair with a cleansing composition before applying the conditioning composition to the hair.

4. The method according to claim 3, further comprising the step of:
drying the hair, with a towel and hair drier, after the conditioning composition is rinsed from the hair.

5. The method according to claim 4, wherein the processing time is at least 3 minutes and no more than 10 minutes.

6. The method according to claim 1, wherein the at least one cationic surfactant is selected from a compound of the general formula

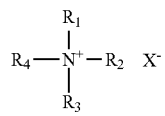

where $R_1$ is a saturated or unsaturated, branched or non-branched alkyl chain with 8-22 C atoms or $$R_5CONH(CH_2)_n$$

where $R_5$ is saturated or unsaturated, branched or non-branched alkyl chain with 7-21 C atoms and n has typical value of 1-4 or $$R_6COO(CH_2)_n$$

where $R_6$ is saturated or unsaturated, branched or non-branched alkyl chain with 7-21 C atoms and n has typical value of 1-4, and $R_2$ is a hydrogen, saturated or unsaturated, branched or non-branched alkyl chain with 1-22 C atoms or $$R_5CONH(CH_2)_n$$

where $R_5$ is saturated or unsaturated, branched or non-branched alkyl chain with 7-21 C atoms and n has typical value of 1-4 or $$R_6COO(CH_2)_n$$

where $R_6$ is saturated or unsaturated, branched or non-branched alkyl chain with 7-21 C atoms or ethoxy or propoxy group with number of ethoxy or propoxy groups varying in the range of 0 to 4 and n has typical value of 1-4, and $R_3$ and $R_4$ are independent from each other H or lower alkyl chain with 1 to 4 carbon atoms, and X is chloride, bromide or methosulfate.

7. The method according to claim 6, wherein the composition further comprises at least one gelling agent and/or at least one thickening agent.

8. The method according to claim 7, wherein the composition further comprises at least one fatty alcohol.

9. The method according to claim 8, wherein the composition further comprises at least one organic solvent.

10. The method according to claim 9, wherein the composition further comprises at least one UV filter.

11. The method according to claim 2, wherein the silicone compounds are selected from linear, cyclic, branched, cross-linked, volatile and non-volatile silicones or their mixtures.

12. The method according to claim 11, wherein the composition further comprises at least one cationic surfactant selected from a compound of the general formula

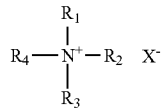

where $R_1$ is a saturated or unsaturated, branched or non-branched alkyl chain with 8-22 C atoms or $$R_5CONH(CH_2)_n$$

where $R_5$ is saturated or unsaturated, branched or non-branched alkyl chain with 7-21 C atoms and n has typical value of 1-4 or $$R_6COO(CH_2)_n$$

where $R_6$ is saturated or unsaturated, branched or non-branched alkyl chain with 7-21 C atoms and n has typical value of 1-4, and and $R_2$, $R_3$ and $R_4$ are independent from each other H or lower alkyl chain with 1 to 4 carbon atoms, and X is chloride, bromide or methosulfate.

13. The method according to claim 12, wherein the composition further comprises at least one gelling agent and/or at least one thickening agent.

14. The method according to claim 13, wherein the composition further comprises at least one fatty alcohol.

15. The method according to claim 14, wherein the composition further comprises at least one organic solvent.

16. The method according to claim 15, wherein the composition further comprises at least one UV filter.

17. The method according to claim 16, wherein the composition further comprises at least one additional conditioning agent selected from oils, cationic polymers and non-ionic compounds.

18. The method according to claim 1, wherein the composition has a pH in a range of 3 to 5.

\* \* \* \* \*